United States Patent
Alkayali (12)

(10) Patent No.: US 6,323,319 B1
(45) Date of Patent: Nov. 27, 2001

(54) METHOD OF MAKING HYDROLYZED COLLAGEN TYPE II

(75) Inventor: Ahmed Alkayali, Laguna Beach, CA (US)

(73) Assignee: Five Continent Enterprise, Inc., Newport Beach, CA (US)

( * ) Notice: Subject to any disclaimer, the term of this patent is extended or adjusted under 35 U.S.C. 154(b) by 0 days.

(21) Appl. No.: 09/453,302

(22) Filed: Dec. 2, 1999

Related U.S. Application Data

(63) Continuation of application No. 08/907,735, filed on Aug. 8, 1997, now Pat. No. 6,025,327.

(51) Int. Cl.$^7$ .............................. C07K 1/12; C07K 14/78
(52) U.S. Cl. ..................... 530/356; 530/407; 530/412; 435/212; 435/273; 514/2
(58) Field of Search .................. 530/344, 356, 530/407, 412; 435/212, 273; 514/2

(56) References Cited

U.S. PATENT DOCUMENTS

| | | |
|---|---|---|
| 4,511,653 | 4/1985 | Play et al. ............................ 435/69 |
| 4,804,745 | 2/1989 | Koepff et al. ...................... 530/356 |
| 5,206,023 | 4/1993 | Hunziker et al. .................... 424/423 |
| 5,364,775 | 11/1994 | Katsumata et al. ................. 435/107 |
| 5,364,845 | 11/1994 | Henderson ............................ 514/54 |
| 5,399,347 | 3/1995 | Trentham et al. ................. 424/184.1 |
| 5,587,363 | 12/1996 | Henderson ............................ 514/54 |
| 5,645,851 | 7/1997 | Moore ................................. 424/439 |

FOREIGN PATENT DOCUMENTS

| | | |
|---|---|---|
| WO 97/254435 | 7/1997 | (WO) . |

OTHER PUBLICATIONS

Barinaga, Treating Arthritis With Tolerance, *Science* 261:1669–1670 (1993).

Bedi et al., Purification and characterization of a collagen-degrading protease from *Porphyromonas gingivalis*, *J. Biol. Chem.* 269:599–606 (1994).

Brucknet et al., *p–HMW–Collegen, a minor collagen obtained from chick embryo cartilage without proteolytic treatment of the tissue*, Eur. J. Biochem.

Cremer et al., *Collagen–Induced Arthritis in Rats: Antigen–Specific Suppression of Arthritis and Immunity By Intravenously Injected Native Type II Collagen*, J. of Immun. 131(6):2995–3000 (1983).

Darnell et al., *Molecular Cell Biology*, Scientific American Books, Inc. New York, NY 1986.

Englert et al., Suppression of Type II Collagen–Induced Arthritis by the Intravenous Adminstration of Type II Collagen or Its Constituent Peptide á$_1$(II)CB$_{10}$, *Cellular Immunology* 87:357–365 (1984).

Fawcett, *A textbook of Histology*, W.B. Ssaunders Co. Philadelphia, PA (1986).

File Caplus on STN: No. 1984:180121. RO 80226, Nov. 30, 1982 Abstract only.

Knauper et al., Biochemical characterization of human collagenase–3, *J. Biol. Chem.* 271:1544–1550 (1996).

New Product Advertisement for "Hydrolyzed Collagen Beauty Supplement", Smarter Nails & Hair, Inc., Newport Beach, CA 92660 (1987).

Stryer, Collagen Has An Unusual Amino Acid Composition And Sequence, *Biochemistry*, Third Edition, W.H. Freeman and Co., New York, p. 262 1988).

Trentham, et al., Autoimmunity to Type II Collagen: An Experimental Model of Arthritis, *J. of Exp. Medicine* 146:857–868 (1977).

Trentham, et al., Effects of Oral Administration of Type II Collagen on Rheumatoid Arthritis, *Science* 261:1727–1730 (1993).

*Primary Examiner*—Christopher S. F. Low
*Assistant Examiner*—Anish Gupta
(74) *Attorney, Agent, or Firm*—Stetina, Brunda, Garred & Brucker

(57) ABSTRACT

Hydrolyzed collagen type II powder compositions, method of preparing the compositions and use of the compositions in treating cartilage defects. The compositions are orally administered to an individual in need of cartilage augmentation in a daily dosage of between about 2,000 and 3,000 mg per day.

8 Claims, 1 Drawing Sheet

METHOD OF MAKING HYDROLYZED COLLAGEN TYPE II

This application is a continuation of U.S. patent application Ser. No. 08/907,735, filed Aug. 8, 1997, now U.S. Pat. No. 6,025,327.

FIELD OF THE INVENTION

The present invention relates to a method of preparing hydrolyzed collagen type II and its use as a therapeutic agent and nutritional supplement.

BACKGROUND OF THE INVENTION

Collagen is a complex structural protein which provides strength and flexibility to skin, hair and nails. Collagen is an essential and major component of muscles, tendons, cartilage, ligaments, joints and blood vessels. There are three main types of collagen: I, II and III. Types I and III are primarily found in skin, tendon and bone. In contrast, type II is found predominantly in particular cartilage. Collagen is an unusual protein, in that the proportion of glycine residues is nearly one-third which is unusually high. Proline is also present to a much greater extent in collagen than in most other proteins. Moreover, collagen contains two amino acids, 4-hydroxyproline and 5-hydroxylysine, that are found in very few other proteins. The amnino acid sequence of collagen is remarkably regular, nearly every third amino acid being glycine. In addition, the sequence glycine-proline-hydroxyproline recurs frequently. In contrast, globular proteins rarely exhibit regularities in their amino acid sequences (Stryer, L., *Biochemistry*, Third Edition, W. H. Freeman and Co., New York, 1.988, pp. 262).

In 1986, collagen was sold for the first time in the United States for use as a food supplement Collagen (a mixture of Types I, II) was extracted from calf skin tissue, hydrolyzed and prepared in powdered form for use as a dietary supplement. The composition was sold under the name "Hydrolyzed Collagen Beauty Supplement™" (Smarter Nails & Hair, Inc., Newport Beach, Calif.). In 1987, "Hydrolyzed, Collagen Beauty Supplement Tablet™" (Smarter Nails & Hair, Inc., Newport Beach, Calif.) was sold which comprised collagen powder and 10 mg vitamin C compressed into 1,000 mg tablets.

U.S. Pat. No. 4,804,745 to Koepff et al. discloses agents containing collagen peptides produced by enzymatic hydrolysis for the treatment of degenerative joint diseases. These peptides can be obtained from animal skin, animal bones and other sufficiently purified connective tissue and have average molecular weights of between 30 and 45 kilodaltons.

U.S. Pat. No. 5,399,347 to Trentham et al. and Trentham et al. (*Science* 261:1727–1729, 1993) disclose the effective treatment of rheumatoid arthritis (RA) with water-soluble whole chick collagen type II or biologically active peptides derived therefrom. The mechanism by which the effect is believed to occur is via oral tolerization to autoantigens.

U.S. Pat. No. 5,364,845 to Henderson discloses a therapeutic composition and method for the protection, treatment and repair of connective tissue in mammals. This composition comprises glucosamine, chondroitin sulfate and manganese ascorbate. U.S. Pat. No. 5,587,363 to Henderson discloses a therapeutic composition and method for the protection, treatment and repair of connective tissue in mammals which includes aminosugars and glycosaminoglycans.

There is a constant need for compositions capable of promoting repair of damaged connective tissue. The present invention addresses this need.

SUMMARY OF THE INVENTION

One embodiment of the present invention is hydrolyzed collagen type II, the hydrolyzed collagen having an average molecular weight of between about 1,500 and 2,500 daltons. Preferably, the hydrolyzed collagen type II has an average molecular weight of about 1,800 daltons. In one aspect of this preferred embodiment, the collagen is obtained from chicken sternal cartilage.

The present invention also provides a method of inducing cartilage formation in an individual with a connective tissue disorder, comprising orally administering to the individual an effective daily cartilage-inducing amount of hydrolyzed collagen type II. The connective tissue disorder includes degenerative joint diseases, joint defects, osteoarthritis, polychondritis, vascular disease and cartilage injuries. Preferably, the effective daily amount is between about 500 and 5,000 mg. More preferably, the effective daily amount is between about 1,000 and 4,000 mg. Most preferably, the effective daily amount is between about 2,000 and 3,000 mg.

Another embodiment of the invention is a method of providing collagen type II as a nutritional supplement, comprising orally administering to an individual a daily dosage of hydrolyzed collagen having an average mole weight of between about 1,500 and 2,500 daltons.

Still another embodiment of the invention is a method of preparing hydrolyzed collagen type II powder, comprising the following steps: cutting fresh chicken sternal cartilage to within not less than about 2 mm of the bone; suspending tho cartilage in an aqueous solution; treating said cartilage with a proteolytic enzyme to form a hydrolysate; sterilizing the hydrolysate; filtering the hydrolysate; concentrating the hydrolysate; and drying the hydrolysate to form a collagen type II powder. The method may further comprise the step of freezing the cartilage after the cutting step. Preferably, the aqueous solution is water. Advantageously, the enzyme is papain, ficin or bromelain. In one aspect of this preferred embodiment, the sterilizing step comprises heating the hydrolysate at 95° C. for about 30 minutes. Preferably, the drying step comprises spray drying. Preferably, the pH of the suspending and treating steps is between about 4 and 8.

DETAILED DESCRIPTION OF THE PREFERRED EMBODIMENTS

Figure 1:
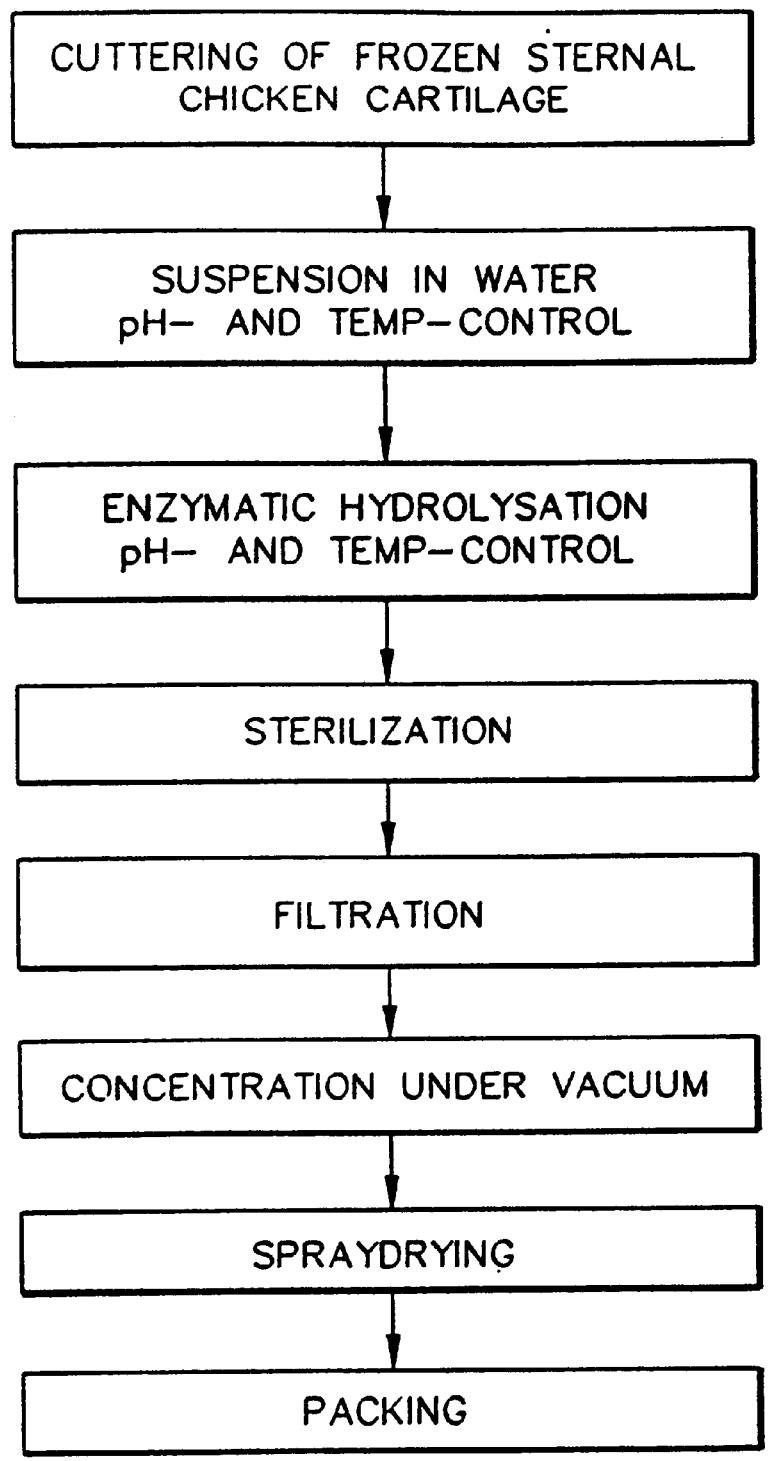
FIG. 1 is a schematic diagram of the process for preparing the hydrolyzed collagen type II powder of the invention.

The present invention provides a hydrolyzed, denatured collagen type II composition, method for preparing the composition and use of the composition in the prevention, treatment and repair of cartilage defects. The method involves cutting fresh sternal cartilage from chicken carcasses and removing all meat therefrom. The sternal cartilage is cut, leaving a space of about two millimeters from the bone so as to not remove any bone fragments. This is critical to the purity of the fmal product because it avoids contamination of collagen type II with types I and III found in bone. The fresh sternal cartilage is then promptly frozen and the remained of the chicken carcass is discarded. It is exclusively the sternal cartilage, cut so no bone is included, that is used for preparing the collagen type II powder. The chicken sternal cartilage is processed according to good manufacturing procedures (GMP). Other contemplated sources of collagen type II are mammalian curfilage (i.e. bovine and porcine) and shark fins.

The production of hydrolyzed collagen type II in powdered form is shown in FIG. 1. Whole cartilage is suspended in an aqueous solution, preferably water for about one hour at about 35° C. at a pH of between about 4 and 8. In a preferred embodiment, the pH is between about 6 and 7. In a more preferred embodiment, the pH is about 6.5. The water is removed, and the cartilage is incubated with one or more proteases obtainable from a natural source (i.e. papain, ficin, bromelain) for between about 2 and 10 hours, preferably about 6 hours, at about 35° C.–55° C. at a pH of between about 4 and 8 to form a hydrolysate. The pH will depend on the pH optimum of the particular enzyme(s) used for the hydrolysis and are well known to one of ordinary skill in the art. The hydrolysate is then sterilized for about 30 minutes at a temperature between about 95° C. and 105° C. The sterilized hydrolysate is filtered through diatomaceous earth, concentrated, preferably under vacuum, dried to form a powder and packed. Other filtration methods are contemplated, including vacuum filtration. In a preferred embodiment, the hydrolyzed collagen type II is spray dried using a size 56 pressure nozzle into a heat tunnel. The final particle size and mesh are adjusted to 0.46 g/cc, yielding a fine powder. The powder is packed in a 40 kg drum with a plastic bag liner. The powder is water soluble.

The average molecular weight of the final product is between 1,500 and 2,500 daltons, preferably 1,800 daltons. The moisture content is between 5% and 7%. The final product is high in mucopolysaccharides, particularly chondroitin sulfate and glucosamine sulfate. The product has 375 calories per 100 grams, contains 67% protein (12.1% total nitrogen), 18% carbohydrate and 0.1% fat. The amino acid composition of the hydrolysate differs substantially from typical collagens and is shown in Table 1. Hydroxyproline is low, hydroxylysine is absent and tryptophan is low. The molecular weight and amino acid composition promote optimal assimilation of the peptides.

TABLE 1

Amino acid composition of hydrolyzed collagen type II

| Amino acid | g/100 g product |
|---|---|
| arginine | 4.42 |
| histidine | 2.05 |
| isoleucine | 1.90 |
| leucine | 4.20 |
| lysine | 3.54 |
| methionine | 1.38 |
| phenylalanine | 2.14 |
| threonine | 2.60 |
| tryptophan | 0.37 |
| alanine | 4.51 |
| asparagine/aspartic acid | 5.29 |
| cystine | 0.46 |
| glutamine/glutamic acid | 8.75 |
| glycine | 8.93 |
| hydroxyproline | 3.90 |
| proline | 5.25 |
| serine | 2.45 |
| tyrosine | 1.16 |
| valine | 2.43 |

When taken orally by an individual with a connective tissue disorder, hydrolyzed collage type II helps build cartilage and significantly improves the disorder. "Oral" administration includes oral, enteral or intragastric administration. The hydrolyzed collagen type II of the invention can be used to treat, for example, degenerative joint diseases (i.e. rheumatoid arthritis), joint defects, osteoarthritis, polychondritis, vascular disease, cartilage injuries, silicone poisoning due to ruptured breast implants, autoimmune diseases involving connective tissue autoantibodies (i.e. rheumatoid arthritis), progressive myopia, Menier's disease and any other connective tissue disorder which would benefit from increased synthesis of cartilage. The hydrolyzed collagen type II also significantly reduces sun-induced skin wrinkles.

For oral administration as a nutritional supplement, therapeutic or prophylactic agent, the hydrolyzed collagen type II of the invention may be provided as a dispersible powder or granule, tablet, aqueous or oil suspension, emulsion, hard or soft capsule, syrup or elixir. Compositions intended for oral use may be prepared according to any method known in the art for the manufacture of pharmaceutical compositions and such compositions may contain one or more of the following agents: sweeteners, flavoring agents, coloring agents and preservatives. The sweetening and flavoring agents will increase the palatability of the preparation. Tablets containing the hydrolyzed collagen type II in admixture with non-toxic pharmaceutically acceptable excipients stable for tablet manufacture are acceptable. Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or may be coated by known techniques to delay disintegration and absorption in the gastrointestinal tract and thereby provide a sustained action over a longer period of time. For example, a time delay material such as glyceryl monostearate or glyceryl distearate alone or with a wax may be employed. The use of enteric coatings is also contemplated.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions may contain the hydrolyzed collage type II of the invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions may be formulated by suspending the active ingredient in a vegetable oil, such as arachis oil, olive oil, sesame oil or coconut oil, or in a mineraloil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These compositions may be preserved by an added antioxidant such as ascorbic acid. Dispersible powers and granules of the invention sable for preparation of am aqueous suspension by the addition of water provide the active ingredient in admixture with a dispersing or wetting agent, a suspending agent, and one or more preservatives. Additional excipients, for example sweetening, flavoring and coloring agents, may also be present.

Syrups and elixirs may be formulated with sweetening agents, such as glycerol, sorbitol or sucrose. Such formulations may also contain a demulcent, a preservative, a flavoring agent and/or a coloring agent.

The hydrolyzed collagen type II powder may be mixed with other ingestible forms and consumed in solid, semisolid solution, suspension or emulsion form. It may also be mixed in conjunction or alternatively with pharmaceutically acceptable carriers, flavor enhancers, water, suspending agents and emulsifying agents. In a preferred embodiment, the hydrolyzed collagen type II powder is mixed with a citrus juice such as orange, grapefruit or tangerine due to the promotion of connective tissue formation by ascorbic acid. The hydrolyzed collagen may also be provided in tablet form in admixture with ascorbic acid.

For use as a nutritional supplement, prophylactic or therapeutic agent, the hydrolyzed collagen is orally administered in a daily dosage of between about 500 mg and 5,000 mg. More preferably, it is administered in a daily dosage of between about 2,000 mg and 4,000 mg. Most preferably, it is administered in a daily dosage of between about 2,000 and 3,000 mg per day. The hydrolyzed collagen type II powder may be formulated into tablets which range from 300 mg to 1,000 mg per tablet. In a preferred embodiment, the hydrolyzed collage type II powder is formulated into 500 mg tablets and 4–6 tablets are taken daily. In another preferred embodiment, the tablets are taken on an empty stomach with a beverage containing vitamin C.

In another preferred embodiment, the hydrolyzed collagen type II powder is mixed with water or a citrus juice prior to ingestion. The preparations described above can be taken indefinitely by individuals affected by connective tissue disorders or by healthy individuals as a preventative agent. If desired, an individual with such a disorder can take the preparation until no further improvement is noted in the disorder.

The above detailed description of the invention is set forth solely to assist in understanding the invention. It is to be understood that variations of the invention, including all equivalents now known or later developed, are to be considered as falling within the scope of the invention, which is limited only by the following claims.

What is claim is:

1. A method for preparing chicken sternal cartilage-derived material comprising hydrolyzed collagen type II powder, comprising the following steps:
   (a) cutting fresh chicken sternal cartilage to within not less than about 2 mm of the bone;
   (b) suspending said cartilage in an aqueous solution;
   (c) treating said cartilage with a proteolytic enzyme to form a hydrolysate, said proteolytic enzyme being capable of hydrolyzing collagen type II to fragments having an average molecular weight of between 1,500 and 2,500 daltons;
   (d) sterilizing said hydrolysate;
   (e) filtering said hydrolysate;
   (f) concentrating said hydrolysate;
   (g) drying said hydrolysate to form a powder enriched in collagen type II; and
   (h) isolating said powder enriched in collagen type II.

2. The method of claim 1, further comprising the step of freezing said cartilage after said cutting step.

3. The method of claim 1, wherein said aqueous solution is water.

4. The method of claim 1, wherein said enzyme is selected from the group consisting of papain, ficin and bromelain.

5. The method of claim 1, wherein said sterilizing step comprises heating said hydrolysate at about 95° C.–105° C. for about 30 minutes.

6. The method of claim 1, wherein said drying step comprises spray drying.

7. The method of claim 1, wherein step (b) is performed at a pH between 4 and 8.

8. The method of claim 1, wherein step (c) is performed at a pH between 4 and 8.

* * * * *